United States Patent [19]

Koethe

[11] Patent Number: 5,005,214
[45] Date of Patent: Apr. 9, 1991

[54] REMOVABLE EYEGLASS SHADE VISOR APPARATUS

[76] Inventor: Terence L. Koethe, 1021 Oakwood Dr., Keller, Tex. 76248

[21] Appl. No.: 442,250

[22] Filed: Nov. 28, 1989

[51] Int. Cl.$^5$ ............................................. A61F 9/04
[52] U.S. Cl. .............................................. 2/13; 2/12; 351/44; 351/47
[58] Field of Search ................. 2/12, 13, 15; 351/44, 351/47

[56] References Cited

U.S. PATENT DOCUMENTS

| | | | |
|---|---|---|---|
| 1,539,805 | 5/1925 | Zellner | 2/13 |
| 1,879,216 | 9/1932 | Hannan et al. | 351/44 |
| 2,052,772 | 9/1936 | Jones | 2/13 |
| 2,106,615 | 1/1938 | Maurer | 2/12 |
| 2,544,221 | 3/1951 | Creighton | 2/13 |
| 2,603,783 | 7/1952 | Gilmartin | 2/13 |
| 2,614,255 | 10/1952 | Ellis | 2/12 |
| 2,620,472 | 12/1952 | Sors et al. | 2/13 |
| 2,640,195 | 6/1953 | Bricker | 2/13 |
| 2,691,165 | 10/1954 | Kane | 2/13 |
| 2,724,834 | 11/1955 | Henderson et al. | 2/13 |
| 2,752,598 | 7/1956 | Abels | 2/13 |
| 2,762,050 | 9/1956 | Bricker | 2/13 |
| 2,795,793 | 6/1957 | Sommers | 2/13 |
| 2,819,468 | 1/1958 | Dincklage | 2/13 |
| 2,891,251 | 6/1959 | Ebersole | 2/13 |
| 3,011,170 | 12/1961 | Lutz | 2/13 |
| 3,237,204 | 3/1966 | Honsaker | 2/13 |
| 3,276,035 | 10/1966 | Jacobson | 2/13 |
| 4,446,571 | 5/1984 | Ross | 2/13 |
| 4,543,667 | 10/1985 | Garbutt | 2/13 |

FOREIGN PATENT DOCUMENTS

398881  9/1933  United Kingdom ............ 2/12

*Primary Examiner*—Werner H. Schroeder
*Assistant Examiner*—Michael A. Neas
*Attorney, Agent, or Firm*—Hubbard, Thurman, Tucker & Harris

[57] ABSTRACT

An elongated, generally strip-like shade visor device is removably attachable to the front frame section of a pair of eyeglasses to shade the wearer's eyes from overhead glare. Support tab portions of the visor project downwardly from its bottom side surface adjacent downturned opposite ends of the visor, each of the support tab portions having a resilient attachment loop removable secured thereto. To install the visor, the outer ends of the eyeglass temple bar members are inserted into the attachment loops, the visor is moved forwardly along the temple bar members, and the attachment loops are stretched diagonally around the outer top corner portions of the front frame section. With the visor mounted in this fashion, a rear side edge of the visor extends above and generally parallel to the top side edge of the front frame section, the front side edge of the visor extends forwardly of the front frame section, and the support tab portions and opposite ends of the visor are pressed rearwardly against the top side of the front frame section to resiliently hold the visor in place.

18 Claims, 2 Drawing Sheets

REMOVABLE EYEGLASS SHADE VISOR APPARATUS

BACKGROUND OF THE INVENTION

The present invention relates generally to shade visor devices which may be removably attached to eyeglass frames to shield the eyeglass wearer's eyes from overhead glare. In a preferred embodiment thereof, the present invention more particularly provides a shade visor which may be easily and quickly mounted on eyeglass frames of widely varying sizes and shapes, without contacting or interfering with the temple portions of the frame, using resilient attachment loops.

Shade visor devices in a variety of shapes and sizes have been previously designed for removable attachment to a top front portion of an eyeglass frame to project forwardly therefrom and shield the wearer's eyes from the glare of overhead sunlight or the like. Numerous attachment structures have been used to removably mount the visor on the eyeglass frame including visor loops which extend around the temple portions of the frame, jaw-type resilient clip members which may be clamped onto an upper front portion of the frame, and interengageable mounting members separately secured to the frame and the visor.

All of the known eyeglass shade visor devices of which the current applicant is presently aware are subject to various limitations and disadvantages, particularly with respect to their frame mounting structures. For example, when attachment loops or other visor mounting structures are secured to the temple portions of the frame, the inward storage folding of the temple members is impeded, thereby making it difficult or impossible to fold up the eyeglasses with the shade visor secured thereto. When jaw-type resilient clip members are secured to the visor for attaching it to the eyeglass frame, the clip members can mar the eyeglass frame if sufficiently tight thereon, or may permit the visor to slide along the frame if it has a very thin configuration. The use of interengageable mounting members separately secured to the eyeglass frame and the shade visor is particularly undesirable due to the necessity of securing one or more of the mounting members directly to the eyeglass frame. This necessity substantially impedes the ability of the particular shade visor to be mounted on another pair of eyeglasses.

In view of the foregoing, it is accordingly an object of the present invention to provide eyeglass shade visor apparatus which eliminates or minimizes the above-mentioned and other limitations and disadvantages of conventional eyeglass shade visor devices.

SUMMARY OF THE INVENTION

In carrying out principles of the present invention, in accordance with a preferred embodiment thereof, improved shade visor apparatus is provided for shielding the eyes of a wearer of eyeglasses from overhead glare, the eyeglasses having a front frame section operatively supporting a pair of lenses, and having a front side, and a top side edge portion with outer top corner portions to which the inner ends of a pair of temple bar members are pivotably secured.

In its preferred embodiment, the shade visor apparatus of the present invention includes an elongated, generally strip-like visor member having a rear side edge portion, a front side edge portion, a bottom side surface, and downturned opposite end portions, the distance between the opposite end portions being somewhat less than the distance between the outer top corner portions of the front frame section of the eyeglasses to which the visor is to be attached. Projecting downwardly from the bottom side surface of the visor are a pair of support tab portions positioned adjacent the opposite ends of the visor, each of the support tab portions having a lower side edge from which a spaced pair of slots inwardly extend. To mount the visor on the front frame section of the eyeglasses, a pair of generally circular elastomeric attachment loop members have circumferentially spaced portions thereon received in the support tab portion slots.

The visor is removably mounted on the eyeglasses by inserting the outer ends of the temple bar members through the circular attachment members, moving the visor member forwardly along the temple bar members, and then diagonally stretching the circular attachment members around the outer top corner portions of the front frame section. The stretched attachment members operatively mount the visor on the front frame section in a position in which the rear side edge of the visor overlies and extends generally parallel to the top side edge portion of the front frame section, the front side edge portion of the visor is positioned forwardly of the front frame section, and the support tab portions and the downturned opposite ends of the visor member are pressed rearwardly against the top side edge portion of the front frame section.

The use of the elastomeric attachment loops connected to the opposite ends of the visor member to mount it on the front frame section of the eyeglasses permits the visor to be easily and quickly attached to eyeglasses of varying shapes and sizes. Additionally, the positioning of the attachment loops around the outer top corners of the front frame section positions the attachment loops so that they do not contact or in any manner interfere with the temple bar members. This permits the temple bar members to be inwardly folded to their usual storage position without the necessity of first removing the visor. Further, the use of the resilient attachment loops prevents the marring of the eyeglass frame, and resiliently but firmly holds the visor member in its operative position on the front frame section, the support tab portions and the opposite end portions of the visor cooperating with the top side edge portion of the front frame section to secure and retain the visor in its eye shading position on the eyeglasses.

DETAILED DESCRIPTION

Figure 1:
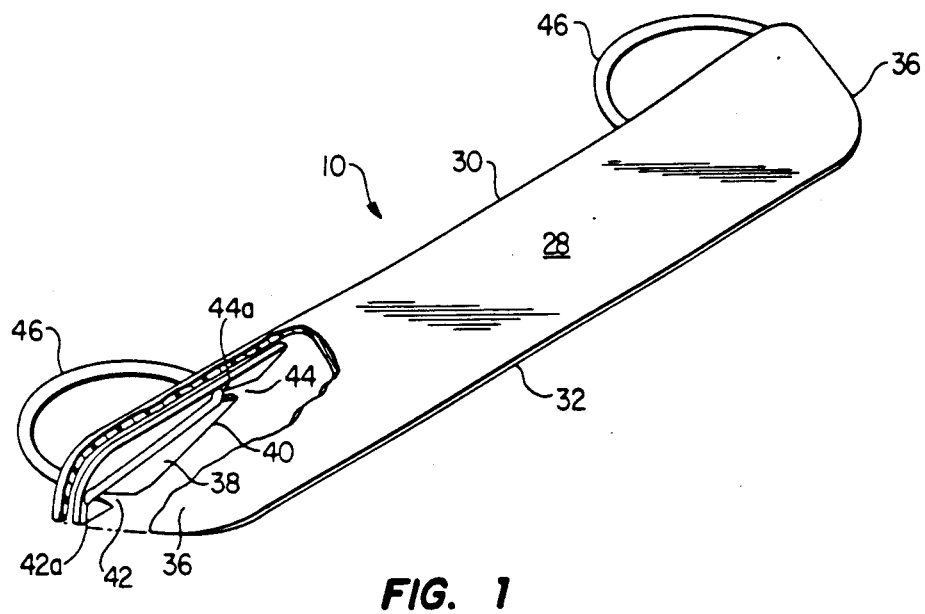
FIG. 1 is a partially cut away perspective view of an eyeglass shade visor device embodying principles of the present invention.
Figure 2:
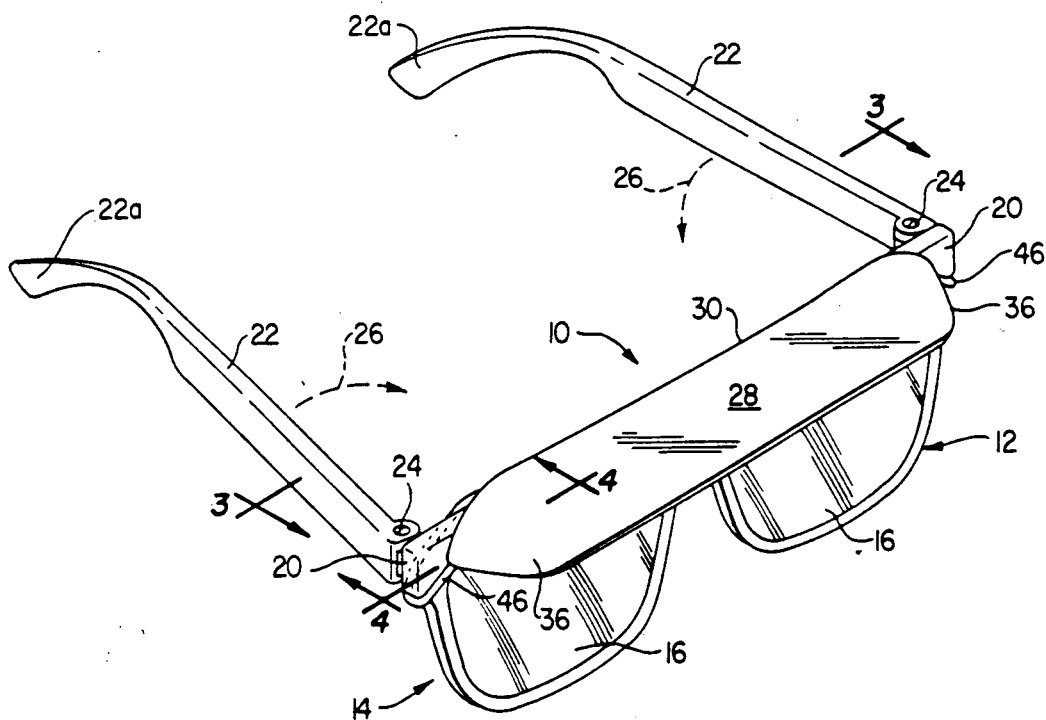
FIG. 2 is a perspective view of the shade visor operatively installed on a representative pair of eyeglasses.

Perspectively illustrated in FIGS. 1 and 2 is a shade visor 10 which embodies principles of the present invention and, in a manner subsequently described, may be removably attached to the front frame section 12 of a representative pair of eyeglasses 14 to shade the eyeglass wearer's eyes from overhead glare. The eyeglasses 14 may be either regular glasses or sunglasses, depending upon whether the lenses 16 supported in the front frame section 12 are clear or tinted.

Referring now to FIGS. 2–5, the front frame section 12 has a top side edge portion 18 which extends between outer top corner portions 20 of the front frame section. The front or inner ends of a pair of elongated temple bar members 22 are pivotly connected, as at 24, to the outer top corner portions 20 of the front frame section 12, the temple bar members having rear or outer ends 22$_a$. In the usual fashion, the temple bar members 22 may be inwardly folded, as indicated by the dotted arrows 26 in FIG. 2, to a storage position in which the temple bar members are positioned generally against and parallel to an upper side portion of the front frame section 12.

Figure 4:
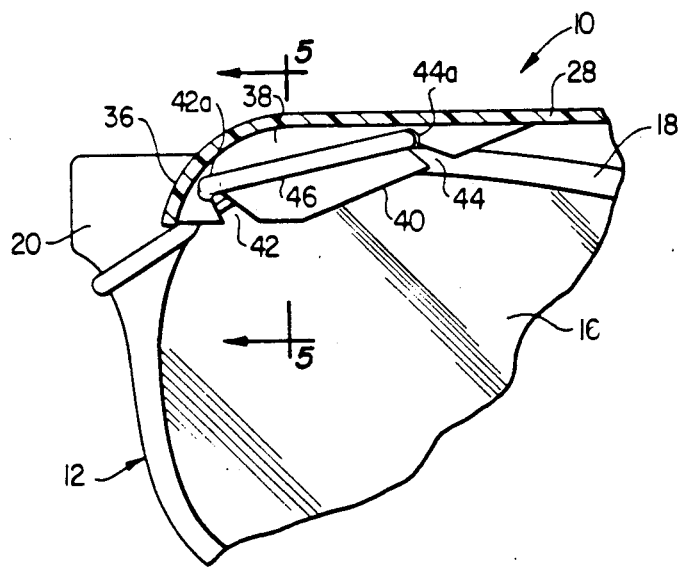
FIG. 4 is an enlarged scale partial cross-sectional view through the eyeglasses and shade visor taken along line 4—4 of FIG. 2.
Figure 5:
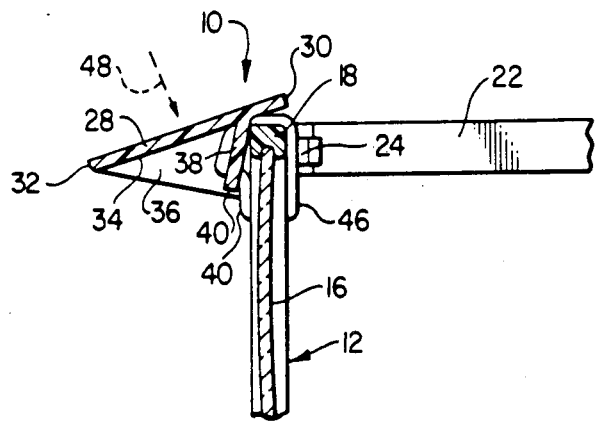
FIG. 5 is a cross-sectional view through the eyeglasses and shade visor taken along line 5—5 of FIG. 4.

The shade visor 10 includes an elongated, generally strip-like injection molded plastic visor member 28 having a rear side edge portion 30, a front side edge portion 32, a bottom side surface 34, and downturned opposite ends 36 which are longitudinally spaced apart a distance somewhat less than the horizontal distance between the outer top corner portions 20 of the front frame section 12. Projecting downwardly from the bottom side surface 34 of the visor member 28, at the opposite visor member ends 36, are a pair of support tab portions 38 which are positioned slightly forwardly of the rear side edge portion 30 (see FIG. 5) and have a bottom side edge 40. Extending inwardly through each of these bottom side edges 40, into their associated support tab portion 38, are a pair of slots 42 and 44 having enlarged, arcuate inner ends 42$_a$ and 44$_a$. As best illustrated in FIG. 4 each of the inner slot ends 44$_a$ is vertically upwardly and horizontally inwardly offset from its associated inner slot end 42$_a$.

Figure 3:
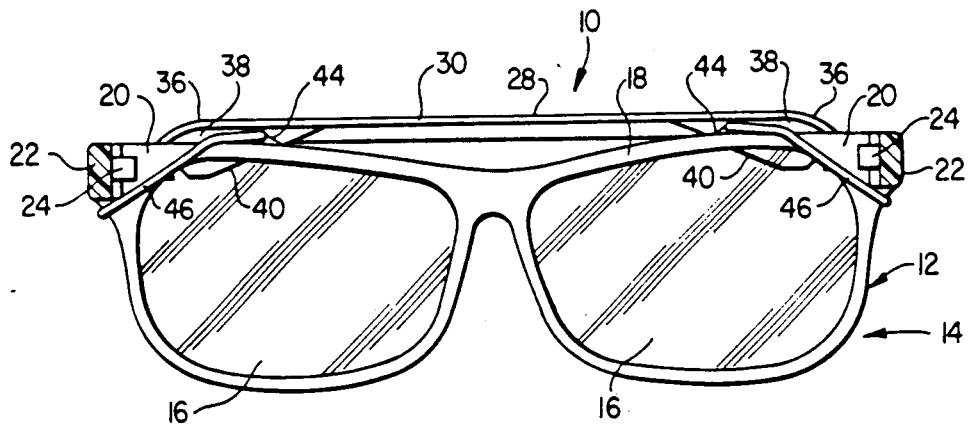
FIG. 3 is an enlarged scale cross-sectional view through the eyeglasses taken along line 3—3 of FIG. 2.

To removably attach the shade visor 10 to the front frame section 12 of the eyeglasses 14, a pair of generally circular, elastomeric attachment loop members 46 are provided. As illustrated in FIG. 1, each of the attachment loop members 46 projects generally rearwardly from the visor member 28, and has circumferentially spaced apart portions which are removably received within one of the support tab portion slot pairs 42, 44. The shade visor 10 is removably mounted on the front frame section 12 by inserting the outer ends 22$_a$ of the temple bar members 22 into the attachment loop members 46, moving the visor member 28 inwardly along the temple bar members 22, and then stretching the attachment loop members 46 generally diagonally around the outer top corner portions 20 of the front frame section 12 as best illustrated in FIGS. 3 and 4, and positioning the support tab portions 38 and the downturned ends 36 of the visor member 38 forwardly of the top side edge portion 18 of the front frame section 12.

With the attachment loop members 46 stretched diagonally around the outer top corner portions 20 in this manner, the downturned visor member ends 36 and the support tab portions 38 are resiliently pressed against the top side edge portion 18 of the front frame section (see FIGS. 3–5) to operatively support the shade visor 10 in a position in which the rear side edge portion 30 of the visor member 28 overlies and extends generally parallel to the top side edge portion 18 of the front frame section 12, and the front side edge portion 32 of the visor member is positioned forwardly and somewhat downwardly of its rear side edge portion 30.

In its installed position, the visor member 28 operates to shade the eyeglass wearer's eyes from overhead glare 48 (FIG. 5) and is resiliently retained in its indicated position by the attachment members 46 which are stretched diagonally around the outer top corner portions 20 of the front frame section 12.

The use of the resilient attachment loop members 46 permits the shade visor 10 to be easily and quickly installed on eyeglasses of varying shapes and sizes without marring their frames, and without the necessity of installing auxiliary attachment devices directly to such frames. Additionally, because the resilient attachment members 46 are stretched around the outer top corner portions 20 of the front frame section, and do not contact the temple bar members 22, the temple bar members may be folded inwardly to their previously described storage orientation without the necessity of removing the visor 10 from the eyeglasses 14. When desired, the shade visor 10 may be quickly removed from the eyeglasses 14 simply by stretching the attachment loop members 46 to move them rearwardly onto the temple bar members 22, moving the visor member 28 rearwardly along the temple bar members, and then simply pulling the resilient attachment loop members 46 rearwardly off the outer ends 22$_a$ of the temple bar members 22.

The visor member 28 and its associated support tab portions 38 may be easily and inexpensively fabricated using a plastic injection molding process, and the visor member 28 may be given an variety of colors which blend in with or sharply contrast to the frame color of the eyeglasses 14. Because of its light weight and relatively small size, the shade visor 10 is additionally quite comfortable to wear and provides the visored eyeglasses with a pleasing appearance.

The foregoing detailed description is to be clearly understood as being given by way of illustration and example only, the spirit and scope of the present invention being limited solely by the appended claims.

What is claimed is:

1. Shade visor apparatus removably securable to a pair of eyeglasses having a front frame section operatively supporting a pair of lenses, said front frame section having a front side, a rear side, and a top side edge portion with outer corner portions to which inner ends of a pair of temple bar members are pivotally secured, said shade visor apparatus comprising:

a visor member having a lower side surface, a front edge portion, a rear edge portion, a pair of opposite end portions, and a pair of support tab portions projecting downwardly from said lower side surface adjacent said opposite end portions; and elastomeric loop means secured to said support tab portions and projecting outwardly therefrom, said elastomeric loop means being operative to be placed over the outer ends of the temple bar members, moved inwardly along the temple bar members, and then stretched around said outer corner portions of said front frame section to removably support said visor member on said front frame section in a position wherein said rear edge portion of said visor member extends generally across said top side edge portion of said front frame section, said front edge portion of said visor member is disposed forwardly of said front frame section, and said support tab portions are pressed against said top side edge portion of said front frame section.

2. The shade visor apparatus of claim 1 wherein:
said support tab portions are positioned forwardly of said rear edge portion of said visor member, and
said elastomeric loop means are operative, when stretched around said outer corner portions of said front frame section, to rearwardly press said support tab portions against said top side edge portion of said front frame section.

3. The shade visor apparatus of claim 1 wherein:
each of said support tab members has a lower side edge, and spaced apart first and second slots extending inwardly from said lower side edge and
said elastomeric loop means include a pair of circular elastomeric members each having circumferentially spaced portions removably received in said first and second slots of one of said support tab members.

4. The shade visor apparatus of claim 3 wherein:
each of said circular elastomeric members projects generally rearwardly from its associated support tab member.

5. The shade visor apparatus of claim 3 wherein:
the inner ends of said first and second slots in each of said support tab members are vertically and horizontally offset from one another.

6. The shade visor apparatus of claim 1 wherein:
said opposite end portions of said visor member are generally downwardly bent, and
said elastomeric loop means, when stretched around said outer corner portions of said front frame section, are additionally operative to press said opposite end portions rearwardly against said top side edge portion of said front frame section.

7. The shade visor apparatus of claim 1 wherein:
said visor member is formed from a plastic material.

8. A shade visor device removably securable to the front frame section of a pair of eyeglasses to shield a wearer of the eyeglasses from overhead glare, the front frame section having a top side edge portion with horizontally spaced outer ends defining outer top corner portions of the front frame section, said shade visor device comprising:
an elongated, generally strip-like shade visor member having a rear side edge portion, a front side edge portion, a pair of opposite end portions, a bottom side surface, and a pair of support tab portions projecting downwardly from said bottom side surface; and
a pair of resilient attachment loop members secured to said support tab portions and positioned to be stretched around said outer top corner portions of said front frame section to removably hold said shade visor member on said front frame section in an operative position wherein said rear side edge portion of said shade visor member overlies and extends generally parallel to said top side edge portion of said front frame section, said front side edge portion of said shade visor member is positioned generally forwardly of said rear side edge portion of said shade visor member, and said support tab portions are pressed rearwardly against said top side edge portion of said front frame section.

9. The shade device of claim 8 wherein:

each of said support tab portions has a lower side edge, and spaced apart first and second slots extending inwardly from said lower side edge, and
each of said attachment members has a generally circular configuration and a pair of circumferentially spaced portions received in the slots of one of said spaced pairs thereof.

10. The shade visor device of claim 9 wherein:
each of said spaced pair of slots has an inner end, the inner ends of each spaced pair of slots being horizontally and vertically offset from one another.

11. The shade visor device of claim 8 wherein:
said pair of opposite end portions of said shade visor member are downwardly bent and positioned and configured to engage the front sides of said outer top corner portions of said front frame section when said shade visor member is in its operative position.

12. The shade visor device of claim 8 wherein:
said shade visor member is formed from a plastic material.

13. Visored eyeglass apparatus comprising:
a pair of eyeglasses having:
a front frame section operatively supporting a pair of lenses and having a top side edge portion, and outer top corner portions, and
a pair of elongated temple bar members having rear ends, and front ends pivotally secured to said outer top corner portions of said front frame section;
an elongated shade visor member having a rear side edge portion positioned above and extending generally parallel to said top side portion of said front frame section, a front side edge portion positioned generally forwardly of said front frame section, and a pair of opposite end portions positioned longitudinally inwardly of said outer top corner portions; and
a pair of elastomeric attachment loop members secured to said opposite end portions of said shade visor members, extending around said outer top corner portions of said front frame section, and laterally pressing a portion of said shade visor member against said front frame section;
said shade visor member having a bottom side surface and a pair of support tab members downwardly extending from said bottom side surface and adjacent said opposite end portions of said shade visor member; and
said elastomeric attachment loop members being secured to said support tab members and pressing them rearwardly against said top side edge portion of said front frame section.

14. The visored eyeglass apparatus of claim 13 wherein:
each of said support tab portions has a lower side edge, and spaced apart first and second slots extending inwardly from said lower side edge, and
each of said pair of attachment loop members has a generally circular relaxed configuration, is stretched around one of said outer top corner portions of said front frame section, and has a pair of circumferentially spaced portions removably received in one of said spaced pair of slots.

15. The visored eyeglass apparatus of claim 13 wherein:
said pair of opposite end portions of said shade visor member are downwardly bent and rearwardly pressed against said front frame section by said elastomeric attachment loop members.

16. The visored eyeglass apparatus of claim 13 wherein:

said eyeglasses are sunglasses.

17. The visored eyeglass apparatus of claim 13 wherein:

said shade visor member is molded from a plastic material.

18. The visored eyeglass apparatus of claim 13 wherein:

said front side edge portion of said shade visor member is positioned downwardly and forwardly apart from said rear side edge portion of said shade visor member.

* * * * *